United States Patent [19]

Kleemann et al.

[11] Patent Number: 5,641,792
[45] Date of Patent: Jun. 24, 1997

[54] BENZOYLGUANIDINES SUBSTITUTED BY HETEROCYCLIC N-OXIDE, PROCESS FOR THEIR PREPARATION AND PHARMACEUTICAL COMPOSITIONS CONTAINING THEM

[75] Inventors: Heinz-Werner Kleemann, Bischofsheim; Hans-Jochen Lang, Hofheim; Jan-Robert Schwark, Frankfurt; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 525,156

[22] Filed: Sep. 8, 1995

[30] Foreign Application Priority Data

Sep. 9, 1994 [DE] Germany ............... 44 32 106.6

[51] Int. Cl.$^6$ ............ A61K 31/44; A61K 31/47; C07D 211/22; C07D 215/60
[52] U.S. Cl. ............ 514/351; 514/312; 514/345; 514/618; 546/153; 546/290; 546/291
[58] Field of Search ............ 546/290, 291, 546/153; 514/351, 618, 345, 312

[56] References Cited

U.S. PATENT DOCUMENTS

| | | | |
|---|---|---|---|
| 3,780,027 | 12/1973 | Cragoe, Jr. et al. | |
| 3,931,181 | 1/1976 | Kompis et al. | |
| 4,233,440 | 11/1980 | Dorlars et al. | 542/458 |
| 4,617,307 | 10/1986 | Browne | 514/300 |
| 4,959,377 | 9/1990 | Effland et al. | 514/349 |
| 5,091,394 | 2/1992 | Englert et al. | 514/331 |
| 5,212,182 | 5/1993 | Musser et al. | 514/314 |
| 5,373,024 | 12/1994 | Lang et al. | 514/618 |

FOREIGN PATENT DOCUMENTS

| | | |
|---|---|---|
| AU52368/93 | 6/1994 | Australia. |
| 602523 | 6/1994 | European Pat. Off.. |
| 271903 | 9/1989 | Germany. |

OTHER PUBLICATIONS

Duff et al., "Antiarrhythmic and Electrophysiologic Actions in Patients With Inducible Sustained Ventricular Tachycardia," Circulation, 79(6):1257–1263 (1989).

Schad et al., "Significance of Left Ventricular Subvalvular Apparatus for Cardiac Performance," Eur. Heart J. (Book of Abstracts), 9(Sup. 1):167 (1988).

English language Derwent Abstract of DD–A–271903. Sep. 1989.

Chemical Abstracts, vol. 77, No. 9, Abstract No. 61765q, "Free Radical Reactions of Aromatic Amine N–oxides, III. Free Radical Arylation of Aromatic Amine N–oxides," Natsume et al. (1972).

Chemical Abstracts, vol. 84, No. 19, Abstract No. 135477r, "Pyridyloxy–phenylalkanoic or pyridyloxybenzoic acid derivatives", Maeda et al. (1976).

Chemical Abstracts, vol. 59, No. 4, Abstract No. 4492e, "Chemical Constitution and Biological Effect of Methylquinolines," Buchmann. (Aug. 1963).

Primary Examiner—Joseé G. Dees
Assistant Examiner—Lily Ledynh
Attorney, Agent, or Firm—Finnegan, Henderson, Farabow, Garrett & Dunner, L.L.P.

[57] ABSTRACT

Benzoylguanidines substituted by heterocyclic N-oxide, process for their preparation, their use as a medicament or diagnostic agent, medicament containing them and intermediate products for their preparation Benzoylguanidines of the formula I

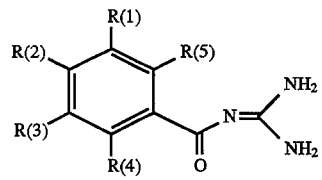

with the meanings given in the text for the substituents, are described.

These are compounds which have an outstanding activity on the cardiovascular system.

8 Claims, No Drawings

BENZOYLGUANIDINES SUBSTITUTED BY HETEROCYCLIC N-OXIDE, PROCESS FOR THEIR PREPARATION AND PHARMACEUTICAL COMPOSITIONS CONTAINING THEM

The invention relates to benzoylguanidines of the formula I

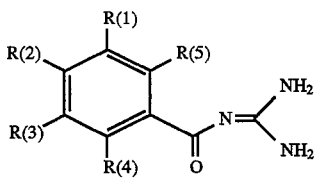

in which:
one of the three substituents R(1), R(2) and R(3) is $(C_1–C_9)$-heteroaryl-N-oxide, which is linked via C or N and is unsubstituted or substituted by 1–3 substituents chosen from the group consisting of F, Cl, $CF_3$, $CH_3$, methoxy, hydroxyl, amino, methylamino and dimethylamino;

or one of the three substituents R(1), R(2) and R(3) is —SR(10), —OR(10), —NR(10)R(11) or —CR(10)R(11)R(12);

R(10) is $—C_aH_{2a}—(C_1–C_9)$-heteroaryl -N-oxide, which is unsubstituted or substituted by 1–3 substituents chosen from the group consisting of F, Cl, $CF_3$, $CH_3$, methoxy, hydroxyl, amino, methylamino and dimethylamino;

a is zero, 1 or 2;

R(11) and R(12) independently of one another are as defined for R(10), hydrogen or $(C_1–C_4)$-alkyl;

and the other particular substituents R(1), R(2) and R(3) independently of one another are $(C_1–C_8)$-alkyl, $(C_2–C_8)$-alkenyl or $—C_mH_{2m}R(14)$;

m is zero, 1 or 2;

R(14) is $(C_3–C_8)$-cycloalkyl or phenyl, which is unsubstituted or substituted by 1–3 substituents chosen from the group consisting of F, Cl, $CF_3$, methyl, methoxy and NR(15)R(16), R(15) and R(16) are hydrogen or $CH_3$;

or the other particular substituents R(1), R(2) and R(3) independently of one another are hydrogen, F, Cl, Br, I, —C≡N, $X—(CH_2)_p—(C_qF_{2q+1})$, R(22)—$SO_u$, R(23)R(24)N—CO, R(25)—CO— or R(26)-R(27)N—$SO_2$—, in which the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are $(C_1–C_8)$-alkyl, $(C_2–C_6)$-alkenyl, $—C_nH_{2n}—R(29)$ or $CF_3$;

n is zero, 1, 2, 3 or 4;

R(28) is hydrogen or $(C_1–C_3)$-alkyl;

R(29) is $(C_3–C_7)$-cycloalkyl or phenyl, which is unsubstituted or substituted by 1–3 substituents chosen from the group consisting of F, Cl, $CF_3$, methyl, methoxy and NR(30)R(31); R(30) and R(31) are hydrogen or $C_1–C_4$-alkyl, or R(23), R(25) and R(26) are also hydrogen;

R(24) and R(27) independently of one another are hydrogen or $(C_1–C_4)$-alkyl;

or

R(23) and R(24), and R(26) and R(27) together are 4 or 5 methylene groups, one $CH_2$ group of which can be replaced by oxygen, S, NH, N—$CH_3$ or N-benzyl;

or the other particular substituents R(1), R(2) and R(3) independently of one another are OR(35) or NR(35)R(36);

R(35) and R(36) independently of one another are hydrogen or $(C_1–C_6)$-alkyl;

or

R(35) and R(36) together are 4–7 methylene groups, one $CH_2$ group of which can be replaced by oxygen, S, NH, N—$CH_3$ or N-benzyl, R(4) and R(5) independently of one another are hydrogen, $(C_1–C_4)$-alkyl, F, Cl, —OR(32), —NR(33)R(34) or $—C_rF_{2r+1}$;

R(32), R(33) and R(34) independently of one another are hydrogen or $(C_1–C_3)$-alkyl;

r is 1, 2, 3 or 4;

and pharmaceutically tolerated salts thereof.

Preferred compounds of the formula I are those in which:

R(1) is $(C_1–C_4)$-alkyl, $(C_2–C_4)$-alkenyl or $—C_mH_{2m}R$ (14), m is zero, 1 or 2;

R(14) is $(C_5–C_6)$-cycloalkyl or phenyl, which is unsubstituted or substituted by 1–2 substituents chosen from the group consisting of F, Cl, $CF_3$, methyl, methoxy and NR(15)R(16); R(15) and R(16) are hydrogen or $CH_3$;

or

R(1) is hydrogen, F, Cl, Br, I, —C≡N, R(22)—$SO_2$, R(23)-R(24)N—CO, R(25)—CO— or R(26)R(27)N—$SO_2$—;

R(22), R(23), R(25) and R(26) independently of one another are $(C_1–C_4)$-alkyl, $(C_2–C_4)$-alkenyl, $—C_nH_{2n}—R(29)$ or $CF_3$;

n is zero, 1 or 2;

R(29) is $(C_5–C_6)$-cycloalkyl or phenyl, which is unsubstituted or substituted by 1–2 substituents chosen from the group consisting of F, Cl, $CF_3$, methyl, methoxy and NR(30)R(31); R(30) and R(31) are hydrogen or methyl;

or

R(23), R(25) and R(26) are hydrogen;

R(24) and R(27) independently of one another are hydrogen or methyl;

or R(23) and (R24) and R(26) and R(27) together are 4 or 5 methylene groups, one $CH_2$ group of which can be replaced by oxygen, S, NH, N—$CH_3$ or N-benzyl;

or

R(1) is OR(35) or NR(35)R(36);

R(35) and R(36) independently of one another are hydrogen or $(C_1–C_4)$-alkyl;

or R(35) and R(36) together are 4–5 methylene groups, one $CH_2$ group of which can be replaced by oxygen, S, NH, N—$CH_3$ or N-benzyl;

one of the substituents R(2) and R(3) is $(C_1–C_9)$-heteroaryl -N-oxide, which is linked via C or N and is unsubstituted or substituted by 1–2 substituents chosen from the group consisting of F, Cl, $CF_3$, $CH_3$, methoxy, hydroxyl, amino, methylamino and dimethylamino;

or one of the substituents R(2) and R(3) is —SR(10), —OR(10), —NR(10)R(11) or —CR(10)R(11)R(12);

R(10) is —$C_aH_{2a}$—($C_1$-$C_9$)-heteroaryl-N-oxide, which is unsubstituted or substituted by 1–2 substituents chosen from the group consisting of F, Cl, $CF_3$, $CH_3$, methoxy, hydroxyl, amino, methylamino and dimethylamino;

a is zero or 1;

R(11) and R(12) are hydrogen or methyl;

and the other particular substituents R(2) and R(3) independently of one another are ($C_1$-$C_4$)-alkyl, hydrogen, F, Cl, Br or I;

R(4) and R(5) independently of one another are hydrogen, methyl, F, Cl, —OR(32), —NR(33)R(34) or $CF_3$;

R(32), R(33) and R(34) independently of one another are hydrogen or methyl;

and pharmaceutically tolerated salts thereof.

Particularly preferred compounds of the formula I are those in which:

R(1) is ($C_1$-$C_4$)-alkyl, ($C_2$-$C_4$)-alkenyl or —$C_mH_{2m}$R (14);

m is zero, 1 or 2

R(14) is ($C_5$-$C_6$)-cycloalkyl or phenyl, which is unsubstituted or substituted by 1–2 substituents chosen from the group consisting of F, Cl, $CF_3$, methyl, methoxy and NR(15)R(16); R(15) and R(16) are hydrogen or $CH_3$;

or

R(1) is hydrogen, F, Cl, Br, I, —C≡N, R(22)—$SO_2$, R(23)R(24)N—CO, R(25)—CO— or R(26)R(27)N—$SO_2$—;

R(22), R(23), R(25) and R(26) independently are methyl or $CF_3$;

or

R(23), R(25) and R(26) are hydrogen;

R(24) and R(27) independently of one another are hydrogen or methyl;

or

R(1) is OR(35) or NR(35)R(36);

R(35) and R(36) independently of one another are hydrogen or ($C_1$-$C_4$)-alkyl;

or

R(35) and R(36) together are 4–5 methylene groups, one $CH_2$ group of which can be replaced by oxygen, S, NH, N—$CH_3$ or N-benzyl, one of the substituents R(2) and R(3) is ($C_1$-$C_9$)-heteroaryl-N-oxide, which is linked via C or N and is unsubstituted or substituted by 1–2 substituents chosen from the group consisting of F, Cl, $CF_3$, $CH_3$, methoxy, hydroxyl and dimethylamino;

or one of the substituents R(2) and R(3) is —SR(10), —OR(10), —NR(10)R(11) or —CR(10)R(11)R(12);

R(10) is ($C_1$-$C_9$)-heteroaryl-N-oxide, which is unsubstituted or substituted by 1–2 substituents chosen from the group consisting of F, Cl, $CF_3$, $CH_3$, methoxy, hydroxyl and dimethylamino;

R(11) and R(12) are hydrogen or methyl;

and the other particular substituent R(2) or R(3) independently of the other is ($C_1$-$C_4$)-alkyl, hydrogen, F, Cl, Br or I;

R(4) and R(5) independently of one another are hydrogen, methyl, F, Cl, —OR(32), —NR(33)R(34) or $CF_3$;

R(32), R(33) and R(34) independently of one another are hydrogen or methyl;

and pharmaceutically tolerated salts thereof.

($C_1$-$C_9$)-heteroaryl are understood as meaning, in particular, radicals which are derived from phenyl or naphthyl in which one or more CH groups are N and/or in which at least two adjacent CH groups are replaced by S, NH or O (to form a five-membered aromatic ring). Furthermore, one or both atoms of the condensation point of bicyclic radicals can also be N atoms (as in indolizinyl).

Heteroaryl-N-oxides are, in particular, imidazolyl-N-oxide, pyrazolyl-N-oxide, triazolyl-N-oxide, tetrazolyl-N-oxide, oxazolyl-N-oxide, isoxazolyl-N-oxide, thiazolyl-N-oxide, isothiazolyl-N-oxide, pyridyl-N-oxide, pyrazinyl-N-oxide, pyrimidinyl-N-oxide, pyridazinyl-N-oxide, indazolyl-N-oxide, quinolyl-N-oxide, isoquinolyl-N-oxide, phthalazinyl-N-oxide, quinoxalinyl-N-oxide, quinazolinyl-N-oxide and cinnolinyl-N-oxide.

If one of the substituents R(1) to R(5) contains one or more centers of asymmetry, these can be in both the S and the R configuration. The compounds can exist as optical isomers, as diastereomers, as racemates or as mixtures thereof.

The alkyl and perfluoroalkyl radicals described can be both straight-chain and branched.

The invention furthermore relates to a process for the preparation of the compounds of the formula I, which comprises reacting a compound of the formula II

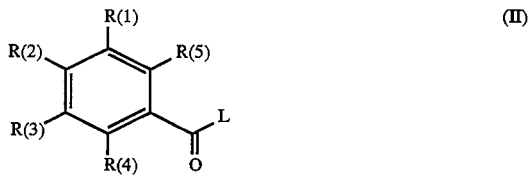

with guanidine, in which L is a leaving group which can easily be substituted nucleophilically.

The activated acid derivatives of the formula II in which L is an alkoxy group, preferably a methoxy group, a phenoxy group, a phenylthio-, methylthio- or 2-pyridylthio group, a nitrogen-containing heterocyclic radical, preferably 1-imidazolyl, are advantageously obtained in a manner known per se from the carboxylic acid chlorides on which they are based (formula II, L=Cl), which in turn can be prepared in a manner known per se from the carboxylic acids on which they are based (formula II, L=OH), for example with thionyl chloride. In addition to the carboxylic acid chlorides of the formula II (L=Cl), other activated acid derivatives of the formula II can be prepared in a manner known per se directly from the benzoic acid derivatives on which they are based (formula II, L=OH), for example the methyl esters of the formula II, where L=$OCH_3$, by treatment with gaseous HCl in methanol, the imidazolides of the formula II by treatment with carbonyldiimidazole (L=1-imidazolyl, Staab, Angew. Chem. Int. Ed. Engl. 1,351–367 (1962)), the mixed anhydrides II with Cl—$COOC_2H_5$ or tosyl chloride in the presence of triethylamine in an inert solvent, and also the activations of benzoic acids with dicyclohexylcarbodiimide (DCC) or with O-[(cyano (ethoxycarbonyl)-methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden 1991]. A number of suitable methods for the preparation of activated carboxylic acid derivatives of the formula II are mentioned with reference to the source literature in J. March, Advanced Organic Chemistry, Third Edition (John Wiley & Sons, 1985), page 350.

The reaction of an activated carboxylic acid derivative of the formula I with guanidine is carried out in a manner known per se in a protic or aprotic polar but inert organic solvent. For the reaction of the benzoic acid methyl esters (II, L=OMe) with guanidine, methanol, isopropanol or THF at between 20° C. and the boiling point of these solvents have proved appropriate. Most of the reactions of compounds II with salt-free guanidine were advantageously carried out in inert solvents such as THF, dimethoxyethane, dioxane or isopropanol. However, water can also be used as the solvent.

If L is Cl, the reaction is advantageously carried out with the addition of an acid-trapping agent, for example in the form of excess guanidine, to bond the hydrohalic acid.

The unknown compounds of the formula II can be prepared by methods known from the literature, for example by converting 4-halo-3-chlorosulfonylbenzoic acids into 3-aminosulfonyl-4-halo-benzoic acids with ammonia or amines, or into 3-alkylsulfonyl-4-halo-benzoic acids with a weak reducing agent, such as sodium bisulfite, and subsequent alkylation, and reacting the products by one of the process variants described above to give compounds I according to the invention.

The introduction of substituted sulfur, oxygen or nitrogen nucleophiles is effected by methods known from the literature for nucleophilic substitution on an aromatic. Halides and trifluoromethanesulfonates have proved suitable as the leaving group on the benzoic acid derivative for this substitution. The reaction is advantageously carried out in a dipolar aprotic solvent, such as, for example, DMF or TMU, at a temperature between 0° C. and the boiling point of the solvent, preferably between 80° C. and the boiling point of the solvent. An alkali metal salt or alkaline earth metal salt having an anion of high basicity and low nucleophilicity, such as, for example $K_2CO_3$ or $CsCO_3$, is advantageously used as the acid-trapping agent.

The alkyl or aryl substituents are introduced by methods known from the literature of palladium-mediated cross-couplings of aryl halides with, for example, organozinc compounds, organostannanes, organoboron acids or organoboranes.

The nitrogen in the heteroaryl substituents is oxidized on suitable intermediate compounds, such as the benzoic acid ester, by methods known in principle. For example, m-chloroperbenzoic acid in an inert solvent, such as methylene chloride, at a temperature of between –30° C. and the boiling point of the solvent has proved appropriate.

The invention also relates to intermediate products of the formula III for the preparation of the compounds I, which intermediate products of the formula III already contain substantial parts of the structure of the compounds I:

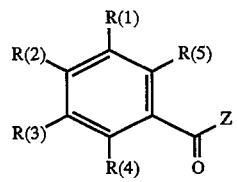

III where

Z is Cl,

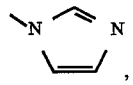,

OR(45), OMet or OH;

R(45) is $(C_1-C_8)$-alkyl or $(C_1-C_4)$-alkylene-phenyl;

Met is an ion of an alkali metal or alkaline earth metal.

These are the acid esters corresponding to the guanidines, the salts and the free acids, which are converted into the guanidines.

Benzoylguanidines I are in general weak bases and can bond acid to form salts. Possible acid addition salts are salts of all the pharmacologically tolerated acids, for example halides, in particular hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride, which is used in treatment as a potassium-saving diuretic. Numerous other compounds of the amiloride type are described in the literature, such as, for example, dimethylamiloride or ethylisopropylamiloride.

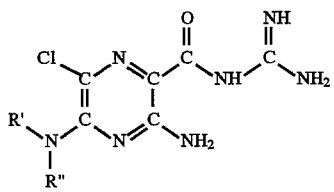

Amiloride: R', R"=H
dimethylamiloride: R', R"=$CH_3$
ethylisopropylamiloride: R'=$C_2H_5$, R"=$CH(CH_3)_2$ Studies have furthermore been disclosed which indicate antiarrhythmic properties of amiloride (Circulation 79, 1257–63 (1989)). However, the facts that this effect is only weak and occurs accompanied by an antihypertensive and saluretic action, and that these side-ffects are undesirable for the treatment of disturbances in cardiac rhythm, opposes widespread use as an antiarrhythmic.

Indications of antiarrhythmic properties of amiloride have also been obtained in experiments on isolated animal hearts [Eur. Heart J. 9 (suppl. 1): 167 (1988) (book of abstracts)]. Thus, for example, it was found on rat hearts that an artificially induced ventricular fibrillation could be suppressed completely by amiloride. The abovementioned amiloride derivative ethylisopropylamiloride was even more potent than amiloride in this model.

Benzoylguanidines which carry a hydrogen atom in the position corresponding to the radical R(1) are described in U.S. Pat. No. 5,091,394 (HOE 89/F 288). German Patent Application P 42 04 575.4 (U.S. Pat. No. 5,373,024) proposes benzoylguanidines in which, however, the substituents do not have the meanings claimed according to the present invention.

Acylguanidines which are structurally similar to the compounds of the formula I and are derived from commercially available loop diuretics, such as bumetanide are claimed in U.S. Pat. No. 3,780,027. A potent salidiuretic activity is reported correspondingly for these compounds.

It was therefore surprising that the compounds according to the invention have no undesirable and adverse salidiuretic properties but very good antiarrhythmic properties which are important in the treatment of diseases such as occur, for example, with oxygen deficiency symptoms. Because of their pharmacological properties, the compounds are outstandingly suitable as antiarrhythmic medicaments having a cardioprotective component for prophylaxis of infarction and infarction treatment and for treatment of angina pectoris, where they also preventively inhibit or greatly reduce the pathophysiological processes during the formation of ischemically induced damage, especially during triggering of ischemically induced cardiac arrhythmias. Because of their protective actions against pathological hypoxic and ischemic situations, the compounds of the formula I according to the invention can be used, as a result of inhibition of the cellular $Na^+/H^+$ exchange mechanism, as medicaments for the treatment of all acute or chronic damage caused by ischemia or diseases thereby induced primarily or secondarily. This applies to their use as medicaments for surgical operations, for example during organ transplants, where the compounds can be used both to protect the organs in the donor before and during removal, to protect removed organs, for example during treatment with or storage thereof in physiological bath fluids, and during transfer to the recipient organism. The compounds are likewise valuable medicaments which have a protective action while angioplastic surgical operations are carried out, for example on the heart and also on peripheral vessels. In accordance with their protective action against ischemically induced damage, the compounds are also suitable as medicaments for the treatment of ischemias of the nervous system, in particular of the central nervous system, where they are suitable, for example, for treatment of apoplexy or cerebral edema. The compounds of the formula I according to the invention furthermore are likewise suitable for treatments of forms of shock, such as, for example allergic, cardiogenic, hyporolemic and bacterial shock.

The compounds of the formula I according to the invention furthermore are distinguished by a potent inhibiting action on the proliferation of cells, for example fibroblast cell proliferation and proliferation of the smooth vascular muscle cells. The compounds of the formula I are thus suitable as valuable therapeutics for diseases in which cell proliferation is a primary or secondary cause, and they can therefore be used as antiatherosclerotics and agents against late diabetic complications, carcinoses, fibrotic diseases, such as pulmonary fibrosis, hepatic fibrosis or renal fibrosis, and organ hypertrophies and hyperplasias, in particular for prostate hyperplasia or prostate hypertrophy.

The compounds according to the invention are effective inhibitors of the cellular sodium/proton antiporter ($Na^+/H^+$ exchanger), which, with numerous diseases (essential hypertension, atherosclerosis, diabetes and the like) is also increased in those cells which are readily accessible for measurements, such as, for example, in erythrocytes, platelets or leukocytes. The compounds according to the invention are therefore suitable as outstanding and simple scientific tools, for example in their use as diagnostic agents for determination of and differentiation between forms of hypertension, and also of atherosclerosis, diabetes, proliferative diseases and the like. The compounds of the formula I are also suitable for preventive treatment to impede the genesis of high blood pressure, for example essential hypertension.

Compared with the known compounds, the compounds according to the invention display a significantly improved water-solubility. They are therefore considerably more suitable for intravenous administration.

Medicaments which comprise a compound I can be administered here orally, parenterally, intravenously or rectally or by inhalation, the preferred administration depending on the particular clinical picture of the disease. The compounds I can be used here by themselves or together with pharmaceutical auxiliaries, both in veterinary and in human medicine.

The expert is familiar with the auxiliaries which are suitable for the desired medicament formulation on the basis of his expert knowledge. In addition to solvents, gel-forming agents, suppository bases, tablet-making auxiliaries and other excipients for active ingredients, it is possible to use, for example, antioxidants, dispersing agents, emulsifiers, defoamers, flavor correctants, preservatives, solubilizing agents or dyestuffs.

For an oral use form, the active compounds are mixed with the additives suitable for this purpose, such as excipients, stabilizers or inert diluents, and are brought into the suitable dosage forms, such as tablets, coated tablets, suppository capsules and aqueous, alcoholic or oily solutions, by the customary methods. Inert excipients which can be used are, for example, gum arabic, magnesia, magnesium carbonate, potassium phosphate, lactose, glucose or starch, in particular corn starch.

Formulation can take place both as dry granules and as moist granules. Possible oily excipients or solvents are, for example, vegetable or animal oils, such as sunflower oil or cod-liver oil.

For subcutaneous or intravenous administration, the active compounds are dissolved, suspended or emulsified, if desired, with the substances customary for this purpose, such as solubilizing agents, emulsifiers or other auxiliaries. Possible solvents are, for example: water, physiological saline solution or alcohols, for example ethanol, propanol and glycerol and in addition also sugar solutions, such as glucose solutions or mannitol solutions, or also a mixture of the various solvents mentioned.

Pharmaceutical formulations which are suitable for administration in the form of aerosols or sprays are, for example, solutions, suspensions or emulsions of the active compound of the formula I in a pharmaceutically acceptable solvent, such as, in particular, example, ethanol or water, or a mixture of such solvents.

If required, the formulation can also comprise other pharmaceutical auxiliaries, such as surfactants, emulsifiers and stabilizers, as well as a propellent gas. Such a formulation usually comprises the active compound in a concentration of about 0.1 to 10, in particular about 0.3 to 3%, by weight.

The dosage of the active compound of the formula I to be administered and the frequency of the administration depend on the action potency and duration of the action of the compounds used; and, furthermore, also on the nature and severity of the disease to be treated and on the sex, age, weight and individual responsiveness of the mammal to be treated.

The daily dose of a compound of the formula I for a patient weighing about 75 kg is on average at least 0.001 mg/kg, preferably 0.01 mg/kg, to not more than 10 mg/kg, preferably 1 mg/kg of body weight. For acute outbreaks of the disease, for example immediately after a cardiac infarction has been suffered, even higher and above all more frequent dosages may also be necessary, for example up to 4 individual doses per day. Up to 200 mg per day may be necessary for intravenous use in particular, for example for an infarction patient on the intensive care ward.

List of Abbreviations

| | |
|---|---|
| MeOH | Methanol |
| DMF | N,N-Dimethylformamide |
| TMU | N,N,N',N'-Tetramethylurea |
| EI | Electron impact |
| DCI | Desorption/chemical ionization |
| RT | Room temperature |
| EA | Ethyl acetate (EtOAc) |
| DIP | Diisopropyl ether |
| MTB | Methyl tert-butyl ether |
| mp | Melting point |

| | |
|---|---|
| HEP | n-Heptane |
| DME | Dimethoxyethane |
| FAB | Fast atom bombardment |
| $CH_2Cl_2$ | Methylene chloride |
| THF | Tetrahydrofuran |
| eq | Equivalent |
| ES | Electrospray ionization |
| Me | Methyl |
| Et | Ethyl |
| Bn | Benzyl |
| CNS | Central nervous system |
| Brine | Saturated aqueous NaCl solution |
| Met | Metal |

Experimental Section

General Instructions For the Preparation of Benzoylguanidines (I)

Variant A: From Benzoic Acids (II, L=OH)

0.01 mol of the benzoic acid derivative of the formula II is dissolved or suspended in 60 ml of anhydrous THF, and 1.78 g (0.011 mol) of carbonyldiimidazole are then added. After the mixture has been stirred at RT for 2 hours, 2.95 g (0.05 mol) of guanidine are introduced into the reaction solution. After the mixture has been stirred overnight, the THF is distilled off under reduced pressure (rotary evaporator), water is added, the pH is brought to 6 to 7 with 2N HCl and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

General Instructions For Preparation of Benzoylguanidines (I)

Variant B: From Benzoic Acid Alkyl Esters (II, L=O-alkyl)

5 mmol of the benzoic acid alkyl ester of the formula II and 25 mmol of guanidine (free base) are dissolved in 15 ml of isopropanol or suspended in 15 ml of THF and the solution or suspension is boiled under reflux until conversion is complete (thin layer monitoring; typical reaction time 2 to 5 hours). The solvent is distilled off under reduced pressure (rotary evaporator), the residue is taken up in 300 ml of EA and the mixture is washed 3 times with 50 ml of $NaHCO_3$ solution each time. It is dried over $Na_2SO_4$, the solvent is distilled off in vacuo and the residue is chromatographed over silica gel using a suitable mobile solvent, for example EA/MeOH 5:1. (For salt formation, cf. Variant A)

EXAMPLE 1

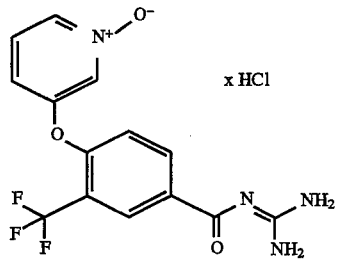

4-(pyridine N-oxide-3-yloxy)-3-trifluoromethyl-benzoylguanidine, hydrochloride 500 mg of 4-(pyridine N-oxide-3-yloxy)-3-trifluoromethylbenzoic acid methyl ester and 472 mg of guanidine are guanylated in 5 ml of isopropanol in accordance with variant B of the general instructions. 250 mg of colorless oil are obtained. M.p. (hydrochloride)=180° C. $R_f$ (EA/MeOH 1:1)=0.27 MS (ES): 341 (M+H)$^+$ a) 4-(pyridine N-oxide-3-yloxy)-3-trifluoromethyl-benzoic acid methyl ester 1.1 g of methyl 4-(3-pyridyloxy)-3-trifluoromethylbenzoate and 912 mg of 3-chloroperbenzoic acid are dissolved in 10 ml of $CH_2Cl_2$ and the solution is stirred at RT for 18 hours. 126 mg of $Na_2SO_3$ are then added and the solvent is removed in vacuo. The residue is taken up in 100 ml of EA and the mixture is extracted once with 100 ml of saturated aqueous $Na_2SO_3$ solution and 3 times with 100 ml of saturated aqueous $Na_2CO_3$ solution each time. The extract is dried over $Na_2SO_4$ and the solvent is removed in vacuo. 1.1 g of a colorless oil are obtained. $R_f$ (EA/MeOH 10:1)=0.19 MS (ES): 314 (M+H)$^+$ b) methyl 4-(3-pyridyloxy)-3-trifluoromethyl-benzoate 2 mmol of methyl 4-fluoro-3-trifluoromethyl-benzoate, 2 mmol of 3-hydroxypyridine and 4 mmol of $K_2CO_3$ are stirred in 15 ml of DMF (anhydrous) at 110° C. for 1.5 hours. The mixture is then poured onto 100 ml of water and extracted 3 times with 50 ml of EA each time. The extract is dried over $Na_2SO_4$, the solvent is removed in vacuo and the product is further reacted without additional purification. 500 mg of colorless oil. $R_f$ (MTB)=0.33 MS (ES): 298 (M+1)

EXAMPLE 2

4-(quinaldine N-oxide-6-yloxy)-3-methylsulfonyl-benzoylguanidine, hydrochloride

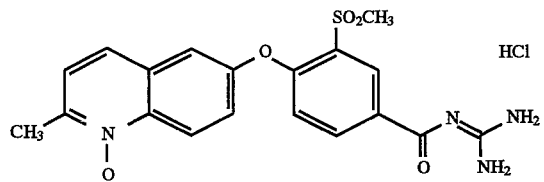

400 mg of 4-(quinaldine N-oxide-6-yloxy)-3-methylsulfonyl-benzoic acid methyl ester and 300 mg of guanidine are guanylated in accordance with the general instructions, variant B, in 15 ml of isopropanol. 140 mg of a vitreous solid are obtained. m.p. (hydrochloride)=247° C. $R_f$ (EE/MeOH 5:1)=0.06 MS (ES): 417 (M+H)$^+$ a) 4-(quinaldine N-oxide-6-yloxy)-3-methylsulfonyl-benzoic acid methyl ester 372 mg of methyl 4-(6-quinaldinyloxy)-3-methylsulfonyl-benzoate are N-oxidized in analogy to Example 1 a) and the product is reacted further without purification.

b) methyl 4-(6-quinaldinyloxy)-3-methylsulfonyl-benzoate 2 g of 6-hydroxyquinaldine, 3.12 g of methyl 4-chloro-3-methylsulfonyl-benzoate and 12.28 g of $Cs_2CO_3$ are stirred in 50 ml of anhydrous tetramethylurea at 110° C. for 1 h. The mixture is cooled, 250 ml of saturated aqueous $NaHCO_3$ solution are added and extraction is carried out 3 times with 125 ml of EA. The extracts are dried over $Na_2SO_4$, the solvent is removed in vacuo and the residue is chromatographed with MTB. 3.98 g of a colorless foam are obtained. $R_f$ (MTB)=0.31 MS (ES): 372 (M+H)$^+$ The compound of Example 3 was synthesized in analogy to Example 2:

EXAMPLE 3

4-(quinaldine N-oxide-6-yloxy)-3-trifluoromethyl-benzoylguanidine, hydrochloride

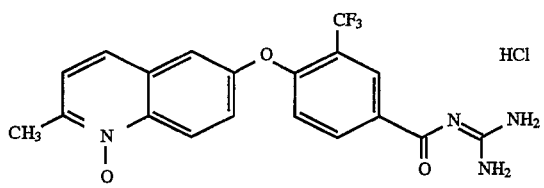

$R_f$ (EA/MeOH 5:1)=0.11 MS (ES): 441 (M+H)$^+$

Pharmacological Data

Inhibition of the Na$^+$/H$^+$ Exchanger of Rabbit Erythrocytes

White New Zealand rabbits (Ivanovas) were given a standard diet with 2% of cholesterol for six weeks in order to activate the Na$^+$/H$^+$ exchange and in this way to be able to determine the Na$^+$ influx into the erythrocytes via Na$^+$/H$^+$ exchange by flame photometry. The blood was removed from the ear arteries and rendered noncoagulable by 25 IU of potassium-heparin. A portion of each sample was used for duplicate determination of the hematocrit by centrifugation. Aliquots of in each case 100 µl were used for measurement of the starting Na$^+$ content of the erythrocytes.

To determine the amiloride-sensitive sodium influx, 100 µl of each blood sample were incubated in 5 ml portions each of a hyperosmolar salt/sucrose medium (mmol/l: 140 NaCl, 3 KCl, 150 sucrose, 0.1 ouabain, 20 tris-hydroxymethylaminomethane) at pH 7.4 and 37° C. The erythrocytes were then washed three times with ice-cold MgCl$_2$/ouabain solution (mmol/l: 112 MgCl$_2$, 0.1 ouabain) and hemolyzed in 2.0 ml of distilled water. The intracellular sodium content was determined by flame photometry.

The Na$^+$ net influx was calculated from the difference between the starting sodium values and the sodium content of the erythrocytes after incubation. The sodium influx which can be inhibited by amiloride resulted from the difference between the sodium content of the erythrocytes after incubation with and without 3×10$^{-4}$ mol/l of amiloride. This procedure was also followed with compounds according to the invention.

Results

Inhibition of the Na$^+$/H$^+$ Exchanger

| Inhibition of the Na$^+$/H$^+$ exchanger: | |
| --- | --- |
| Example | IC$_{50}$ µmol/l |
| 1 | 0.08 |
| 2 | 0.3 |
| 3 | 0.019 |

We claim:

1. A benzoylguanidine of the formula I

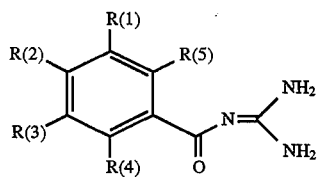

in which:

one of the three substituents R(1), R(2) and R(3) is a (C$_1$–C$_9$)-heteroaryl-N-oxide derived from phenyl or naphthyl in which one or more CH groups are N and/or in which at least two adjacent CH groups are replaced by S, NH, or O, which is linked via C or N and is unsubstituted or substituted by 1–3 substituents chosen from the group consisting of F, Cl, CF$_3$, CH$_3$, methoxy, hydroxyl, amino, methylamino and dimethylamino;

or one of the three substitutents R(1), R(2) and R(3) is —SR(10), —OR(10), —NR(10)R(11) or —CR(10)R(11)-R(12);

R(10) is —C$_a$H$_{2a}$—(C$_1$–C$_9$)-heteroaryl-N-oxide derived from phenyl or naphthyl in which one or more CH groups are N and/or in which at least two adjacent CH groups are replaced by S, NH, or O, which is unsubstituted or substituted by 1–3 substituents chosen from the group consisting of F, Cl, CF$_3$, CH$_3$, methoxy, hydroxyl, amino, methylamino and dimethylamino;

a is zero, 1 or 2;

R(11) and R(12) independently of one another are as defined for R(10), hydrogen or (C$_1$–C$_4$)-alkyl;

and the other particular substituents R(1), R(2) and R(3) independently of one another are (C$_1$–C$_8$)-alkyl, (C$_2$–C$_8$)-alkenyl or —C$_m$H$_{2m}$R(14);

m is zero, 1 or 2;

R(14) is (C$_3$–C$_8$)-cycloalkyl or phenyl, which is unsubstituted or substituted by 1–3 substituents chosen from the group consisting of F, Cl, CF$_3$, methyl, methoxy and NR(15)R(16), R(15) and R(16) are hydrogen or CH$_3$;

or the other particular substituents R(1), R(2) and R(3) independently of one another are hydrogen, F, Cl, Br, I, —C≡N, X—(CH$_2$)$_p$—(C$_q$F$_{2q+1}$), R(22)—SO$_u$, R(23)R(24)N—CO, R(25)—CO— or R(26)R(27)N—SO$_2$—, in which the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently of one another are (C$_1$–C$_8$)-alkyl, (C$_2$–C$_6$)-alkenyl, —C$_n$H$_{2n}$—R(29) or CF$_3$;

n is zero, 1, 2, 3 or 4;

R(28) is hydrogen or (C$_1$–C$_3$)-alkyl;

R(29) is (C$_3$–C$_7$)-cycloalkyl or phenyl, which is unsubstituted or substituted by 1–3 substituents chosen from the group consisting of F, Cl, CF$_3$, methyl, methoxy and NR(30)R(31);

R(30) and R(31) are hydrogen or C$_1$–C$_4$-alkyl, or R(23), R(25) and R(26) are also hydrogen;

R(24) and R(27) independently of one another are hydrogen or (C$_1$–C$_4$)-alkyl;

or

R(23) and R(24), and R(26) and R(27) together are 4 or 5 methylene groups, one CH$_2$ group of which can be replaced by oxygen, S, NH, N—CH$_3$ or N-benzyl;

or the other particular substituents R(1), R(2) and R(3) independently of one another are OR(35) or NR(35)R(36);

R(35) and R(36) independently of one another are hydrogen or $(C_1-C_6)$-alkyl;

or

R(35) and R(36) together are 4–7 methylene groups, one $CH_2$ group of which can be replaced by oxygen, S, NH, N—$CH_3$ or N-benzyl, R(4) and R(5) independently are hydrogen, $(C_1-C_4)$-alkyl, F, Cl, —OR(32), —NR(33)R(34) or —$C_rF_{2r+1}$;

R(32), R(33) and R(34) independently are hydrogen or $(C_1-C_3)$-alkyl;

r is 1, 2, 3 or 4;

and pharmaceutically tolerated salts thereof.

2. A compound of the formula I as claimed in claim 1, in which:

R(1) is $(C_1-C_4)$-alkyl, $(C_2-C_4)$-alkenyl or —$C_mH_{2m}R$ (14), m is zero, 1 or 2;

R(14) is $(C_5-C_6)$-cycloalkyl or phenyl, which is unsubstituted or substituted by 1–2 substituents chosen from the group consisting of F, Cl, $CF_3$, methyl, methoxy and NR(15)R(16); R(15) and R(16) are hydrogen or $CH_3$;

or

R(1) is hydrogen, F, Cl, Br, I, —C≡N, R(22)—$SO_2$, R(23)R(24)N—CO, R(25)—CO— or R(26)R(27)N—$SO_2$—;

R(22), R(23), R(25) and R(26) independently are $(C_1-C_4)$-alkyl, $(C_2-C_4)$-alkenyl, —$C_nH_{2n}$—R(29) or $CF_3$;

n is zero, 1 or 2;

R(29) is $(C_5-C_6)$-cycloalkyl or phenyl, which is unsubstituted or substituted by 1–2 substituents chosen from the group consisting of F, Cl, $CF_3$, methyl, methoxy and NR(30)-R(31);

R(30) and R(31) are hydrogen or methyl;

or

R(23), R(25) and R(26) are hydrogen;

R(24) and R(27) independently of one another are hydrogen or methyl;

or R(23) and (R24), and R(26) and R(27) together are 4 or 5 methylene groups, one $CH_2$ group of which can be replaced by oxygen, S, NH, N—$CH_3$ or N-benzyl;

or

R(1) is OR(35) or NR(35)R(36);

R(35) and R(36) independently of one another are hydrogen or $(C_1-C_4)$-alkyl;

or R(35) and R(36) together are 4–5 methylene groups, one $CH_2$ group of which can be replaced by oxygen, S, NH, N—$CH_3$ or N-benzyl;

one of the substituents R(2) and R(3) is a $(C_1-C_9)$-heteroaryl-N-oxide derived from phenyl or naphthyl in which one or more CH groups are N and/or in which at least two adjacent CH groups are replaced by S, NH, or O, which is linked via C or N and is unsubstituted or substituted by 1–2 substituents chosen from the group consisting of F, Cl, $CF_3$, $CH_3$, methoxy, hydroxyl, amino, methyl-amino and dimethylamino;

or one of the substituents R(2) and R(3) is —SR(10), —OR(10), —NR(10)R(11) or —CR(10)R(11)-R(12);

R(10) is a —$C_aH_{2a}$—$(C_1-C_9)$-heteroaryl-N-oxide derived from phenyl or naphthyl in which one or more CH groups are N and/or in which at least two adjacent CH groups are replaced by S, NH, or O, which is unsubstituted or substituted by 1–2 substituents chosen from the group consisting of F, Cl, $CF_3$, $CH_3$, methoxy, hydroxyl, amino, methylamino and dimethylamino;

a is zero or 1;

R(11) and R(12) are hydrogen or methyl;

and the other particular substituents R(2) and R(3) are independently of one another $(C_1-C_4)$-alkyl, hydrogen, F, Cl, Br or I;

R(4) and R(5) independently of one another are hydrogen, methyl, F, Cl, —OR(32), —NR(33)R(34) or $CF_3$ R(32), R(33) and R(34) independently of one another are hydrogen or methyl.

3. A compound of the formula I as claimed in claim 1, in which:

R(1) is $(C_1-C_4)$-alkyl, $(C_2-C_4)$-alkenyl or —$C_mH_{2m}R$ (14);

m is zero, 1 or 2;

R(14) is $(C_5-C_6)$-cycloalkyl or phenyl, which is unsubstituted or substituted by 1–2 substituents chosen from the group consisting of F, Cl, $CF_3$, methyl, methoxy and NR(15)-R(16);

R(15) and R(16) are hydrogen or $CH_3$;

or

R(1) is hydrogen, F, Cl, Br, I, —C≡N, R(22)—$SO_2$, R(23)R(24)N—CO, R(25)—CO— or R(26)R(27)N—$SO_2$—;

R(22), R(23), R(25) and R(26) independently of one another are methyl or $CF_3$;

or

R(23), R(25) and R(26) are hydrogen;

R(24) and R(27) independently of one another are hydrogen or methyl;

or

R(1) is OR(35) or NR(35)R(36);

R(35) and R(36) independently of one another are hydrogen or $(C_1-C_4)$-alkyl;

or

R(35) and R(36) together are 4–5 methylene groups, one $CH_2$ group of which can be replaced by oxygen, S, NH, N—$CH_3$ or N-benzyl, one of the substituents R(2) and R(3) is a $(C_1-C_9)$ heteroaryl-N-oxide derived from phenyl or naphthyl in which one or more CH groups are N and/or in which at least two adjacent CH groups are replaced by S, NH, or O, which is linked via C or N and is unsubstituted or substituted by 1–2 substituents chosen from the group consisting of F, Cl, $CF_3$, $CH_3$, methoxy, hydroxyl and dimethylamino;

or one of the substituents R(2) and R(3) is —SR(10), —OR (10), —NR(10)R(11) or —CR(10)R(11)-R(12); R(10) is $(C_1-C_9)$-heteroaryl-N-oxide derived from phenyl or naphthyl in which one or more CH groups are N and/or in which at least two adjacent CH groups are replaced by S, NH, or O, which is unsubstituted or substituted by 1–2 substituents chosen from the group consisting of F, Cl, $CF_3$, $CH_3$, methoxy, hydroxyl and dimethylamino;

R(11) and R(12) independently of one another are hydrogen or methyl;

and the other particular substituents R(2) and R(3) independently of one another are $(C_1-C_4)$-alkyl, hydrogen, F, Cl, Br or I;

R(4) and R(5) independently of one another are hydrogen, methyl, F, Cl, —OR(32), —NR(33)R(34) or $CF_3$;

R(32), R(33) and R(34) independently of one another are hydrogen or methyl.

4. A process for the preparation of a compound of the formula I as claimed in claim 1, which comprises reacting a compound of the formula II

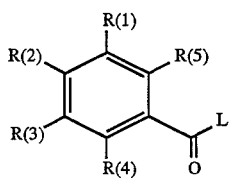
(II)

in which R(1) to R(5) have the meanings given in claim 1, with guanidine, in which L is a leaving group which can easily be substituted nucleophilically.

5. A pharmaceutical composition for the treatment of arrhythmias, which comprises a compound of formula I as claimed in claim 1 together with a pharmaceutically acceptable carrier.

6. A pharmaceutical composition for use in surgical operations and organ transplants, which comprises a compound of formula I as claimed in claim 1 together with a pharmaceutically acceptable carrier.

7. A pharmaceutical composition for the treatment of cardiac infract, angina pectoris, ischemic heart conditions, ischemic conditions of the peripheral and central nervous systems, of apoplexy, of peripheral organs and limbs, and of states of shock, which comprises a compound of formula I was claimed in claim 1 together with a pharmaceutically acceptable carrier.

8. A method for the treatment or prophylaxis of ischemic conditions of the heart, peripheral organs and limbs, the peripheral and central nervous system or of stroke, comprising administering an effective amount of a compound of the formula I as claimed in claim 1.

* * * * *